United States Patent [19]

Zaitsev et al.

[11] 4,225,676

[45] Sep. 30, 1980

[54] METHOD OF PREPARING NUTRIENT MEDIUM FROM LITTER-FREE LIQUID MANURE FOR CULTIVATING MICROORGANISMS AND A PLANT FOR REALIZING SAME

[75] Inventors: Konstantin P. Zaitsev, Moscow; Mikhail S. Shleizer, Moldavskaya SSR; Svirid I. Voronevsky, Kishinev; Vasily D. Reshetnik, Kishinev; Lazar I. Vain, Kishinev; Vladimir V. Movchan, Moldavskaya SSR; Alexandr S. Kishlar, Moldavskaya SSR; Fagim K. Kireev, Moldavskaya SSR; Vsevolod S. Somov; Larisa K. Alferova, both of Moscow, all of U.S.S.R.

[73] Assignee: Moskovsky Tekhnologichesky Institut Myasoni I Molochnoi Promysh Lennosti, U.S.S.R.

[21] Appl. No.: 825,430

[22] Filed: Aug. 17, 1977

[51] Int. Cl.² ............................................. A23K 1/00
[52] U.S. Cl. ................................. 435/255; 435/243; 435/256; 435/942; 426/62; 426/807
[58] Field of Search ............... 195/33, 100, 102, 139, 195/143; 426/60, 62, 623, 630, 635, 636, 478, 486, 487, 495, 511, 521, 476, 480, 492, 807, 626; 71/15, 21; 210/2, 11, 15, 65, 71

[56] References Cited

U.S. PATENT DOCUMENTS

| | | | |
|---|---|---|---|
| 3,375,116 | 3/1968 | Anthony | 71/21 |
| 3,860,487 | 1/1975 | Emanuel | 195/100 |
| 3,865,568 | 2/1975 | Kratzer | 71/21 |
| 3,875,319 | 4/1975 | Seckler et al. | 426/478 |
| 4,018,899 | 4/1977 | Seckler et al. | 426/657 |
| 4,119,495 | 10/1978 | Belyaev et al. | 210/18 |

*Primary Examiner*—R. B. Penland
*Attorney, Agent, or Firm*—Steinberg and Blake

[57] ABSTRACT

According to the proposed method, the starting material is separated into concentrated suspension and clarified liquid fraction. The concentrated suspension is heated and hydrolyzed under excess pressure in the presence of a mineral acid as a catalyst. The clarified liquid fraction of the starting material is sterilized and mixed with the hydrolysate. The mixture is then neutralized to the required pH. The neutralized mixture is then separated from harmful volatile admixtures and cooled to obtain nutrient medium suitable for cultivating microorganisms. To separate the starting material into concentrated suspension and clarified liquid fraction, to hydrolyze the concentrated suspension, to sterilize the clarified liquid fraction of the starting material, to mix the hydrolysate with the sterilized clarified liquid and to neutralize the mixture, to remove harmful volatile substances from the neutralized mixture and to cool the final neutralized mixture to prepare nutrient medium for cultivating microorganisms, the plant is provided with the appropriate devices and vessels. In order to mix the sterilized liquid fraction of the starting material with the hydrolysate and subsequently to neutralize the mixture, the sterilizer is connected with the device for separation of the starting material and the neutralization tank; and in order to hydrolyze the concentrated suspension use is made of a hydrolyzer having a closed cylinder, lined on the inside with a heat- and acid-resistant material. Connections are mounted on the hydrolyzer for delivery of concentrated suspension and a mineral acid, for delivery of heating steam into the lower part of the apparatus, for discharging the hydrolyzate from the hydrolyzer, and for releasing excess steam from the hydrolyzer.

8 Claims, 3 Drawing Figures

METHOD OF PREPARING NUTRIENT MEDIUM FROM LITTER-FREE LIQUID MANURE FOR CULTIVATING MICROORGANISMS AND A PLANT FOR REALIZING SAME

The present invention relates to methods of preparing nutrient media from inedible vegetable materials for cultivating microorganisms, and plants for realizing these methods, and more particularly it relates to a method of preparing nutrient medium from litter-free liquid manure for cultivating microorganisms, and to a plant for realizing this method.

Known in the prior art is a method of preparing nutrient medium from litter-free liquid manure for growing microorganisms. According to this method, the starting material is separated on a centrifuge, or by settling, into concentrated suspension and clarified liquid fraction. The clarified liquid is sterilized and used as a fertilizer.

The concentrated suspension is first heated and delivered into a hydrolysis apparatus, where the suspension is hydrolysed in the presence of a catalyst, viz., mineral acid. The hydrolysate is neutralized to the required pH, freed from harmful volatile substances, and cooled. The thus prepared nutrient medium can be used for cultivating microorganisms.

The disadvantage of the method is that a considerable part of the nutrient substances contained in the starting material passes into the clarified liquid and is not utilized in the nutrient medium.

The object of this invention is to provide a method of preparing nutrient medium from litter-free liquid manure for cultivating microorganisms, that would increase the output of the nutrient medium.

This and other objects of the invention have been attained in a method of preparing nutrient medium from litter-free liquid for cultivating microorganisms in which the starting material is separated into concentrated suspension and clarified liquid fraction, the latter is sterilized, whereas the concentrated suspension is heated and hydrolysed under excess pressure in the presence of a mineral acid, as a catalyst; the obtained hydrolysate is neutralized to the required pH and harmful volatile substances are removed. The hydrolysate is cooled to give a nutrient medium suitable for cultivating microorganisms.

According to the present invention, the hydrolysate is mixed with the sterilized liquid fraction before neutralization.

This invention, consisting in the method of preparing nutrient medium from litter-free liquid manure for cultivating microorganisms, provides conditions for complete utilization of organic and mineral substances, contained in fresh manure, in the form of fodder yeast for animals and fertilizers.

It is recommended that the neutralized hydrolysate be separated from sludge so that fodder yeast obtained by cultivating microorganisms on such sludge-free nutrient medium could be given not only to ruminants, but also to animals with one-cavity stomach (such as pigs) and poultry.

A plant is known for cultivating microorganisms on nutrient medium obtained from litter-free liquid manure by the known method. It consists of a collecting vessel provided with a stirrer into which the starting material is delivered from the animal housing, a device for separating the starting material into concentrated suspension and clarified liquid fraction, an apparatus for hydrolysis of the concentrated suspension, a sterilizer for the clarified liquid fraction of the starting material, connected with the device for separating the starting material into concentrated suspension and clarified liquid fraction, a vessel, with a stirrer, for neutralization of the hydrolysate, a device for removal from the neutralized hydrolysate of harmful volatile substances, and a heat-exchanger for cooling the neutralized hydrolysate to obtain a nutrient medium suitable for cultivating microorganisms. All these units are connected into a flow-line.

The disadvantage of the described plant is that the clarified liquid fraction is not utilized, and that the known hydrolyser is not effective for the purpose. Moreover, the known hydrolyser is expensive and complicate in manufacture and maintenance. The working pressure of the known hydrolyser is to 20 atm. It is a cylinder provided with upper and lower throats. The upper throat is provided with a lid which is opened mechanically to load the apparatus through the upper throat. The lid is then closed before the hydrolysis is started. The operations of opening and closing the lid are controlled remotely by an electric motor. A flange-adapter is connected to the lower throat of the hydrolyser. A fast-acting unloading valve is connected to the flange. A special device opens the valve to discharge the sludge and then closes it. A filtering device intended to separate the hydrolysate is installed inside the hydrolyser. The hydrolysate is discharged from the apparatus through the lower connection.

A man-hole, 500 mm in diameter, is provided in the cylindrical part of the hydrolyser, through which the servicing personnel can get inside the apparatus for repair and any other operations whenever required.

A loading mechanism, located above the upper throat of the hydrolyser is used to load the starting materials into the apparatus.

As seen from the above description, the design of the hydrolyser is quite complicated; its manufacture requires much metal, it is expensive, and is not very effective in the hydrolysis of concentrated suspension obtained from litter-free liquid manure.

Another object of the invention is to remove said disadvantages in the known plant for preparing nutrient medium from litter-free liquid manure for cultivating microorganisms.

It is the specific object of the invention to provide additional communication between the units of the plant and to alter the design of the hydrolyser so as to provide a plant for preparing nutrient medium from litter-free liquid manure for microorganisms, that would be more effective in operation and simpler in design, and would be cheaper compared with the known plants used for the same purpose.

The proposed plant incorporates into a flow-line: a collecting tank, with a stirrer, for the starting material, a device for separating the starting material into concentrated suspension and clarified liquid fraction, an apparatus for hydrolysis of the concentrated suspension, a sterilizer for the clarified liquid fraction of the starting material, a vessel provided with a stirrer intended for neutralization of the hydrolysate, a device intended for removal of harmful volatile substances from the neutral hydrolysate, and a heat exchanger intended to cool the neutralized hydrolysate to give nutrient medium suitable for cultivating microorganisms. According to the invention, the vessel for neutralized hydrolysate is connected with the sterilizer to accept the sterilized clarified liquid fraction of the starting materials, whereas the apparatus intended for hydrolysis of concentrated suspension has a closed cylinder lined on the inside with an acid- and heat-resistant material; the apparatus is provided with connections for the inlet for concentrated suspension and mineral acid, for the outlet of the hydrolysate, and connection for delivery of heating steam into the lower part of the apparatus, and a connection intended to release excess steam, mounted in the upper part of the apparatus.

The proposed invention provides a plant for preparing nutrient medium from litter-free liquid manure for cultivating microorganisms, which is effective in operation and is simpler and cheaper than the known plants used for the same purpose.

It is recommended that a settling tank should be installed between the neutralization tank and a device for removal of harmful volatile substances from the neutralized hydrolysate, and connected with both apparatuses; the settling device is intended to remove the sludge and this makes it possible to cultivate fodder yeast on the nutrient medium free from the sludge. Thus prepared yeast can be used to feed poultry and animals with one-cavity stomach (pigs).

For a better understanding of the invention it is illustrated by a description of its exemplary embodiment and the appended drawings in which.

Figure 1:
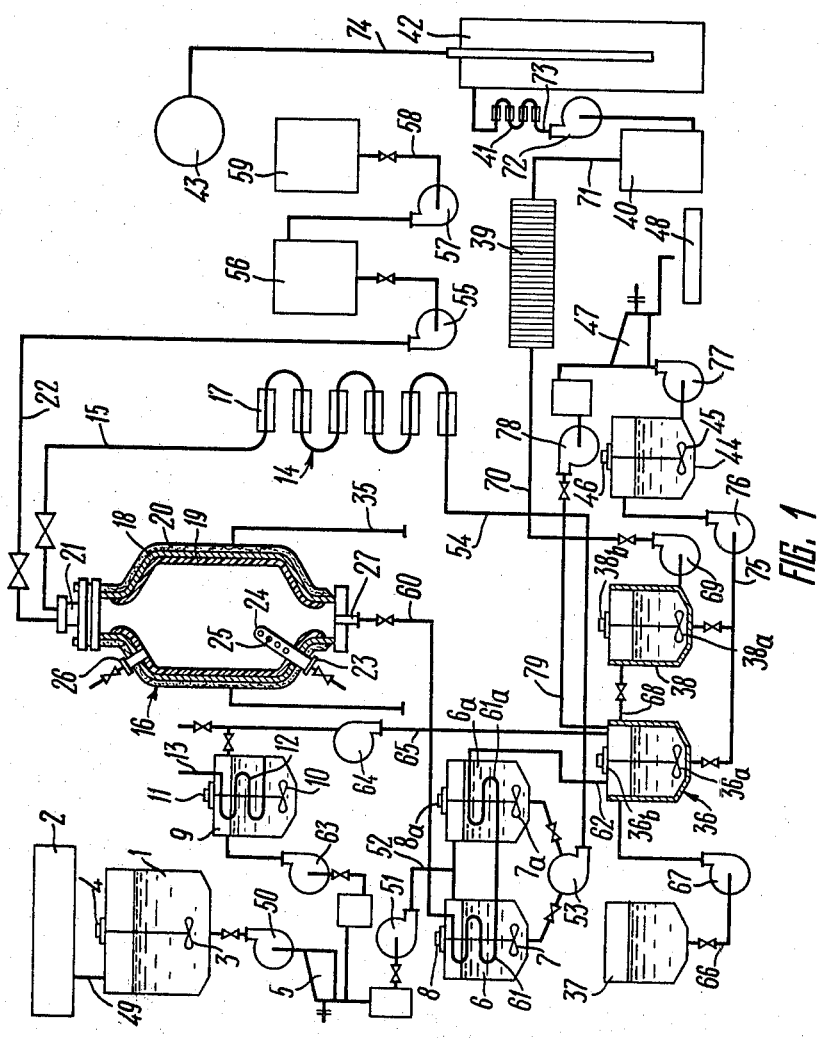
FIG. 1 is a schematic diagram of a plant for preparing nutrient medium of microorganism (fodder yeast) cultivation, from litter-free liquid manure, in which the sludge is removed from the neutralized hydrolysate.

The plant has a collecting tank 1 (FIG. 1) intended for liquid manure (the starting material) that is delivered from animal housing 2. The collecting tank 1 is provided with a stirrer 3, driven by an electric motor 4. The starting material is homogenized in the collecting tank 1.

The filtering centrifuge 5 separates the homogenized starting material into a clarified liquid fraction and concentrated suspension.

Reinforced concrete vessels 6 and 6a are intended to store concentrated suspension. The vessels are provided with stirrers 7 and 7a driven from motors 8 and 8a.

Vessel 9 is intended to collect the clarified liquid fraction of the starting material, and also to sterilize it; the vessel 9 is provided with a stirrer IO driven by a motor 11. A steam-heated coil 12 is installed in the vessel 9 and is intended to heat the clarified liquid fraction. Steam is delivered into the coil 12 through pipeline 13 from a boiler plant, which is not shown in the figure.

The concentrated suspension is preheated to a temperature of 80°-100° C. in a double-tube (shell-and-tube) heat exchanger 14. The concentrated suspension is delivered into the apparatus 16 through the inner tube 15, whereas steam is passed into the outer tube 17.

Figure 2:
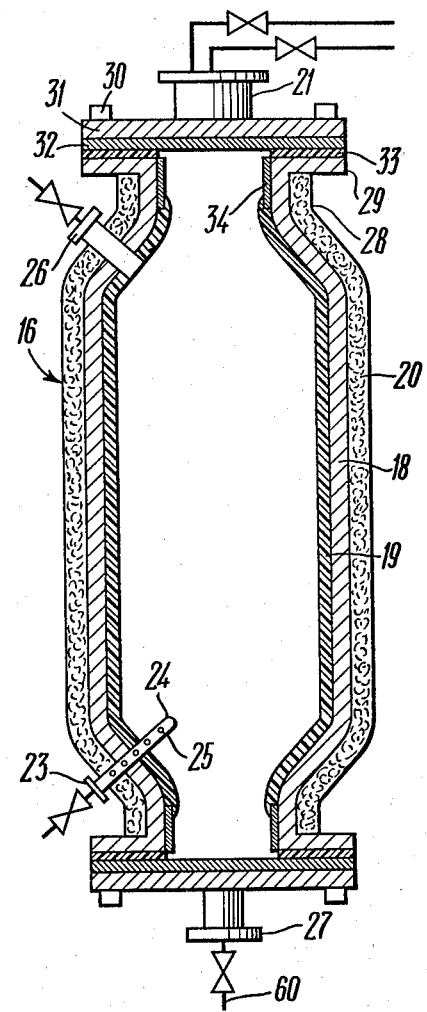
FIG. 2 shows the apparatus for hydrolysis of concentrated suspension.

The heated concentrated suspension is hydrolysed in the apparatus 16. The hydrolyser 16 (FIG. 2) has a closed metallic cylinder 18, the interior of which is lined with an acid- and heat-resistant material, consisting of a concrete layer and a heat- and acid-resistant brick. The housing 18 is insulated on the outside with sovelite tiles (glass wool) 20.

Connection 21 is mounted in the upper part of the apparatus and is intended to deliver preheated concentrated suspension and sulphuric acid into the hydrolyser. Pipe 15 delivers the preheated suspension and pipe 22, sulphuric acid.

Steam is delivered into the lower part of the hydrolyser 16 through connection 23. A sparger, which is actually an acid-resistant pipe 24 with perforations 25, is used to deliver steam into the apparatus. The sparger is mounted inside the connection 23.

Connection 26 mounted in the upper part of the apparatus serves to release excess steam.

Connection 27 serves to discharge hydrolysed concentrated suspension from the apparatus 16.

The hydrolyser 16 is provided with a throat 28 and a flange 29, bolted to which is a steel disc 31. This manhole is intended to provide access for servicing personnel into the hydrolyser for repair or any other operations whichever may be required. The disc 31 is lined with copper 32 on its interior surface. A sealing gasket 33 of acid-resistant rubber is placed between the flange 29 and the disc 31. The throat of the apparatus 28 is protected from corrosion by a bronze sleeve 34 built into the acid-proof lining 19. The hydrolyser 16 is installed on supports 35 in the vertical position.

Connection 21, intended to deliver preheated concentrated suspension and sulphuric acid into the upper part of the hydrolyser, is mounted through the agency of disc 31.

The hydrolysate is neutralized in a vessel 36 provided with a stirrer 36a, driven from an electric motor 36 b. Sterilized clarified liquid fraction of the starting material is also delivered into the vessel 36 from the vessel 9. The clarified liquid fraction partly neutralizes the hydrolysate. To neutralize the hydrolysate to the required pH, ammonia water is delivered into the vessel 36 from vessel 37.

The neutralized hydrolysate is divided into clarified liquid and sludge in a settling tank 38 provided with a stirrer 38a, driven from an electric motor 38b.

Harmful volatile substances are removed from the neutralized mixture in an ultraviolet irradiation device 39.

The neutralized hydrolysate, freed from harmful volatile substances is collected in a stand-by vessel 40.

The neutralized hydrolysate freed from harmful volatile substances is finally cooled in a heat exchanger 41 to prepare a nutrient medium suitable for cultivating microorganisms.

Microorganisms are cultivated in a vat 42, where the medium is aerated by air delivered by a blower 43.

Sludge obtained in the vessel 36 and settling tank 38 is collected in a receptacle 44 provided with a stirrer 45 driven from a motor 46.

The sludge is delivered from the receptacle 44 onto a centrifuge 47 where it is separated into the liquid and solid phase. The solid fraction is loaded onto the transport facility 48 that carries it away for further utilization as fertilizer, and other purposes, whereas the liquid phase is delivered into the vessel 36.

The plant for preparing nutrient medium from litter-free liquid manure for cultivating microorganisms (fodder yeast) operates as follows.

Liquid manure is delivered from live-stock housing 2 into a collecting tank 1 through pipe-line 49. A stirrer 3 installed in the collecting tank 1 homogenizes the manure.

The homogenized mass is fed by a pump 50 onto a centrifuge 5, that separates the starting material into concentrated suspension and liquid fraction.

The concentrated suspension is fed by a pump 51, through line 52, into vessels 6 and 6a, from where it is fed by a pump 53, through pipe-line 54, and heat exchanger 14, into a hydrolyser 16 through its connection 21. Sulphuric acid is fed into the hydrolyser through the same connection 21, (through pipe-line 22) by a pump 55, from an intermediate vessel 56 into which it is fed by a pump 57, through pipe-line 58, from a stand-by vessel 59.

The concentrated suspension is preheated in the heat exchanger 14 and then heated in the hydrolyser 16, to a temperature of 125°–130° C., by steam fed into the hydrolyser 16 through the lower connection 23. The material is kept at this temperature for 2.5–3 hours.

The valve of the connection 27 is then opened and the hydrolysate is discharged from the hydrolyser into line 60 and further into coils 61 and 61a, where it is preliminarily cooled.

The precooled hydrolysate flows by gravity through line 62 into the vessel 36 where it is neutralized.

The liquid fraction of the starting material clarified on the centrifuge 5 is fed by a pump 63 into a sterilizer 9 where it is sterilized. The sterilized liquid fraction is fed by a pump 64, through line 65, into the vessel 36 where it is also neutralized by mixing with the hydrolysate. The hydrolysate is partly neutralized by the sterile clarified liquid fraction, which is alkaline.

To neutralize the mixture to the required pH, ammonia water is added to it through line 66 from a vessel 37 by a pump 67.

Part of the sludge is precipitated from the mixture in the vessel 36 by settling.

The neutralized hydrolysate is then delivered into a settling tank 38 from the vessel 36 through line 68. The sludge is finally precipitated from the mixture in the settling tank 38 and the clarified neutralized liquid is thus obtained.

The clarified neutralized liquid is fed by a pump 69, through line 70, onto a unit 39 for ultraviolet irradiation to remove harmful volatile substances from the neutralized liquid The neutralized liquid, freed from harmful volatile substances, is fed by gravity through line 71 into a stand-by vessel 40.

From this vessel, the neutralized liquid is fed by a pump 72 through line 73, into vat 42, where microorganisms (fodder yeast) are grown. The liquid passes through a heat exchanger 41, where it is cooled to the required temperature.

Pure culture of fodder yeast is also delivered into the vat 42.

The nutrient medium is aerated in the vessel 42 by air delivered by a blower 43 through line 74.

From the vessel 36, where the hydrolysate is neutralized, and from the settling tank 38, the sludge is delivered by a pump 76 into a vessel 44.

From the vessel 44, the sludge is further fed by a pump 77 onto a centrifuge 47.

The liquid fraction separated on the centrifuge 47 is fed by a pump 78, through line 79, into the vessel 36, where the hydrolysis is neutralized, whereas the solid fraction is discharged onto a transporting facility 48 that carries it away for utilization as fertilizers, or for some other purposes.

The neutralized liquid is cooled in the heat exchanger 41 to a temperature within the range of 32°–40° C., which is optimum for cultivation of fodder yeast.

Cultivation of yeast is carried out by the known methods, commonly used in industry.

Yeast grown in the vat 42 is delivered onto a separator (not shown in the drawing), where yeast is thickened, and the thickened suspension is then sterilized to prepare a product that can be used in the liquid state for feeding animals. The thickened suspension can be dried to prepare dry fodder.

Figure 3:
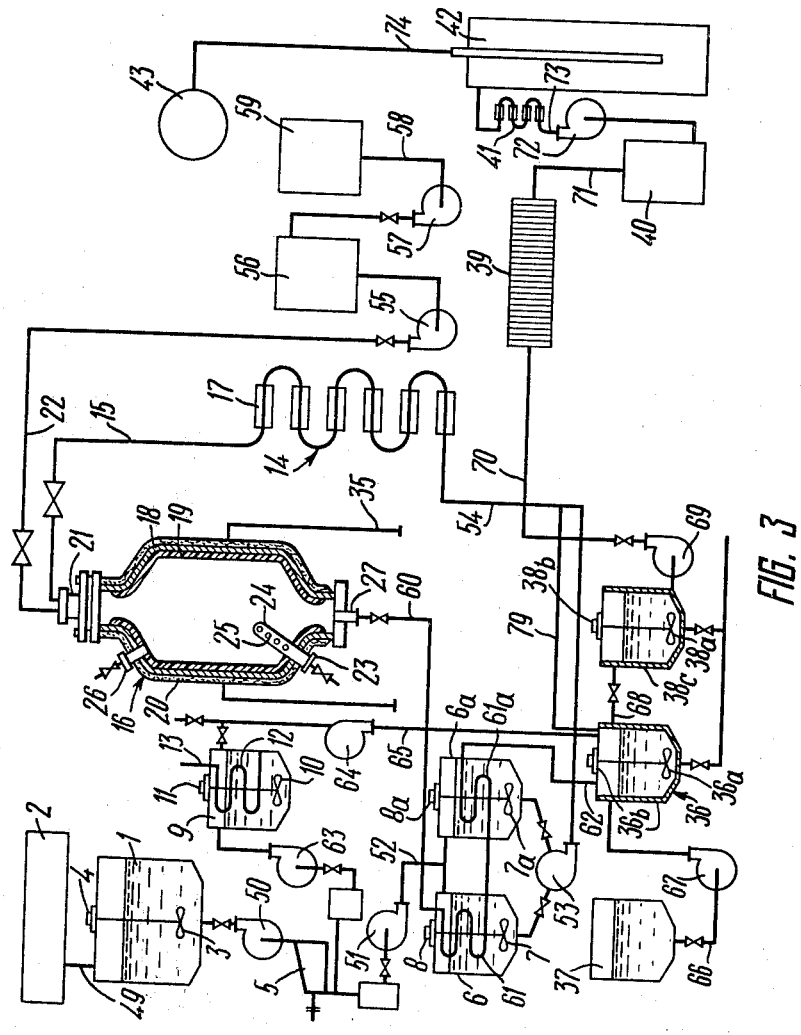
FIG. 3 is a schematic diagram of a plant for preparing nutrient medium for microorganism (fodder yeast) cultivation, from litter-free liquid manure, wherein the sludge is not removed from the neutralized hydrolysate.

If the nutrient medium is used for the manufacture of fodder yeast, intended to be fed to ruminants (large cattle), the process can be simplified. In this case the neutralized liquid (see FIG. 3), from the vessel 38c, which in this case is a simple vessel, without precipitating the sludge from the liquid, is delivered onto the unit 39 for ultraviolet irradiation to remove harmful volatile substances.

The neutralized liquid, freed from harmful admixtures, is fed by gravity (as in the case with preparing nutrient medium by the first variant) into a stand-by vessel 40, and the process for preparing fodder yeast is continued as described above.

Preparing nutrient medium without removal of the sludge from the neutral liquid significantly cheapens the product.

The problem of complete utilization of manure at large animal breeding farms arises in connection with the production of meat on an industrial scale.

At present utilization of manure is based on the existing method of waste disposal, where feces are decontaminated by the biological method in settling reservoirs of varying capacity or in aerated tanks.

But the organic components of manure are destroyed by this method and it loses its fertilizing properties. Moreover, this method of utilization of manure, contradicts the principles of sanitation, hygiene and protection of the environment.

The proposed method and the plant for preparing nutrient medium from litter-free liquid manure for cultivating microorganisms provides complete utilization of both the concentrated suspension and the liquid fraction from manure or the gut stills of slaughtered cattle and poultry at large animal and poultry farms or meat packing plants.

The proposed method and plant make it possible to utilize the organic and mineral compounds contained in manure, and to improve the econimical effect of its use, compared with the known methods and plants of similar purpose.

The calculations show that if the whole mass of manure is utilized, that is concentrated suspension and the clarified part used for preparing nutrient medium for cultivating fodder yeast, a farm raising 108,000 pigs a year can produce over 2000 tons of additional fodder yeast (10 percent moisture content) annually.

Feeding pigs on yeast (source of proteins and vitamins) ensures the production of additional 1000 tons of pork a year (as live weight).

Well-balanced rations on farms utilizing manure by the proposed method ensure about 10–20 percent savings.

The annual requirements for fodder on a farm producing 108,000 pigs a year, is about 52,000 tons. It follows therefore that 5.2 thousand tons of fodder can be saved with the proposed method.

The economy will be even more appreciable if the mother solutions are utilized as fertilizers.

Processing of manure at animal farm having the capacity of 108,000 pigs a year is effected in a special shop located on the territory of the farm, and this decreases the area of the farm 2-3 times (as compared with the area of farms treating manure by the prior-art methods).

The experience with utilization of the proposed method and plant for preparing nutrient medium from litter-free liquid manure for cultivating microorganisms (yeast) has shown that owing to utilization of the clarified liquid fraction in preparing nutrient medium, the yield of fodder yeast increases significantly.

The requirements for alkali to neutralize the hydrolysate decreases 20-30 percent, because the clarified liquid fraction of the starting material is used for the purpose.

The cost of the hydrolyser in the proposed plant is three times less than the cost of the hydrolyser used in the known plants.

We claim:

1. A method for preparing a nutrient medium for microorganism cultivation from litter-free liquid manure, the method comprising the steps of
    separating the liquid manure into a concentrated suspension fraction and a clarified liquid fraction;
    heating and hydrolyzing, under excess pressure and in the presence of a mineral acid catalyst, the concentrated suspension fraction to form a hydrolysate;
    sterilizing the clarified liquid fraction;
    mixing the hydrolysate with the sterilized liquid fraction to form a hydrolysate mixture;
    neutralizing the hydrolysate mixture to a required pH; and
    removing harmful volatile substances from the neutralized mixture by ultraviolet radiation, whereby a neutralized mixture is formed which is suitable for the use as a nutrient medium for cultivating microorganisms.

2. The method of claim 1, wherein any sludge from the neutralized hydrolysate mixture is separated prior to the removal of harmful volatile substances.

3. A method for preparing a nutrient medium for microorganism cultivation from litter-free liquid manure, comprising the steps of:
    separating liquid manure into a concentrated suspension fraction and a clarified liquid fraction;
    heating and hydrolyzing the concentrated suspension fraction in a sealed vessel, heated by steam to a temperature in the range of 125°-130° C., and under excess pressure in the presence of a mineral acid catalyst, to form a hydrolysate mixture;
    sterilizing the clarified liquid fraction;
    mixing the hydrolysate with the sterilized liquid fraction to partially neutralize the hydrolysate and to form a hydrolysate mixture;
    neutralizing the hydrolysate mixture; and
    removing harmful volatile substances from the neutralized mixture by ultraviolet radiation, whereby a neutralized mixture is formed which is suitable for use as a nutrient for the cultivation of fodder yeast.

4. The method of claim 3 wherein the concentrated suspension is maintained at temperature in said sealed vessel for a period of two and one half-three hours.

5. The method of claim 4 wherein the mineral acid catalyst is sulphuric acid.

6. The method of claim 5 wherein the hydrolysate mixture is neutralized with ammonia water.

7. The method of claim 6 comprising in addition separating any sludge material from the neutralized hydrolysate mixture.

8. The method of claim 4 comprising, in addition, cooling the neutralized mixture to a temperature suitable for the cultivation of microorganisms; and mixing the thus cooled neutralized hydrolysate mixture with a microorganism culture, and cultivating the microorganism in the cooled liquid.

* * * * *